United States Patent [19]
Scott et al.

[11] Patent Number: 5,527,313
[45] Date of Patent: Jun. 18, 1996

[54] BIPOLAR SURGICAL INSTRUMENTS

[75] Inventors: Ian M. Scott, Ridgefield; H. Jonathan Tovey, Milford, both of Conn.

[73] Assignee: United States Surgical Corporation, Norwalk, Conn.

[21] Appl. No.: 418,130

[22] Filed: Apr. 6, 1995

Related U.S. Application Data

[63] Continuation of Ser. No. 232,309, Apr. 25, 1994, abandoned, which is a continuation of Ser. No. 122,319, Sep. 17, 1993, abandoned, which is a continuation of Ser. No. 949,581, Sep. 23, 1992, abandoned.

[51] Int. Cl.$^6$ .................................................. A61B 17/39
[52] U.S. Cl. .................................. 606/51; 606/52; 606/41
[58] Field of Search ........................... 606/41, 42, 45–52, 606/205–208; 607/115, 116

[56] References Cited

U.S. PATENT DOCUMENTS

| | | | |
|---|---|---|---|
| 1,813,902 | 7/1931 | Bovie | 606/52 |
| 3,643,663 | 2/1972 | Sutter . | |
| 3,920,021 | 11/1975 | Hiltebrandt | 606/51 |
| 3,938,527 | 2/1976 | Rioux et al. . | |
| 4,003,380 | 1/1977 | Wien . | |
| 4,005,714 | 2/1977 | Hiltebrandt | 606/51 |
| 4,014,343 | 3/1977 | Esty . | |
| 4,016,881 | 4/1977 | Rioux et al. . | |
| 4,041,952 | 8/1977 | Morrison, Jr. et al. | 606/52 |
| 4,074,718 | 2/1978 | Morrison, Jr. | 606/51 |
| 4,076,028 | 2/1978 | Simmons . | |
| 4,202,337 | 5/1980 | Hren et al. . | |
| 4,228,800 | 10/1980 | Degler, Jr. et al. . | |
| 4,311,145 | 1/1982 | Esty et al. . | |
| 4,370,980 | 2/1983 | Lottick | 606/42 |
| 4,418,692 | 12/1983 | Guay | 606/45 |
| 4,625,723 | 12/1986 | Altnether et al. . | |
| 4,655,216 | 4/1987 | Tischer . | |
| 4,674,499 | 6/1987 | Pao . | |
| 4,732,149 | 3/1988 | Sutter . | |
| 4,760,848 | 8/1988 | Hasson . | |
| 4,823,791 | 4/1989 | D'Amelio et al. . | |
| 4,869,717 | 9/1989 | Adair | 604/51 |
| 4,890,610 | 1/1990 | Kirwan, Sr. et al. . | |
| 4,938,761 | 7/1990 | Ensslin . | |
| 4,985,030 | 1/1991 | Melzer et al. . | |
| 5,009,656 | 4/1991 | Reimels . | |
| 5,026,370 | 6/1991 | Lottick . | |
| 5,078,717 | 1/1992 | Parins et al. . | |
| 5,116,332 | 5/1992 | Lottick . | |
| 5,147,357 | 9/1992 | Rose et al. . | |
| 5,147,378 | 9/1992 | Markham . | |
| 5,197,964 | 3/1993 | Parins . | |
| 5,222,973 | 6/1993 | Sharpe et al. . | |
| 5,258,006 | 11/1993 | Rydell et al. . | |

FOREIGN PATENT DOCUMENTS

| | | |
|---|---|---|
| 0513962 | 11/1992 | European Pat. Off. . |
| 0517244A1 | 12/1992 | European Pat. Off. . |
| 0518230A1 | 12/1992 | European Pat. Off. . |
| 2310137 | 12/1976 | France . |
| 2680314A1 | 2/1993 | France . |
| 2325626 | 11/1974 | Germany . |
| 2734847 | 2/1979 | Germany . |

*Primary Examiner*—Stephen C. Pellegrino
*Assistant Examiner*—Michael Peffley

[57] ABSTRACT

A bipolar surgical instrument is disclosed comprising a handle and a tool for applying electrical energy to body tissue. In a preferred embodiment, the tool is forceps having jaws movable between open and closed positions in response to movement of the handle. A pair of electrical connection receptacles in the handle respectively connect to a pair of electrically isolated conducting paths. Each path contacts a forceps jaw for transmitting electrical energy to body tissue. The instrument has particular application to endoscopic and laparoscopic surgical procedures.

31 Claims, 7 Drawing Sheets

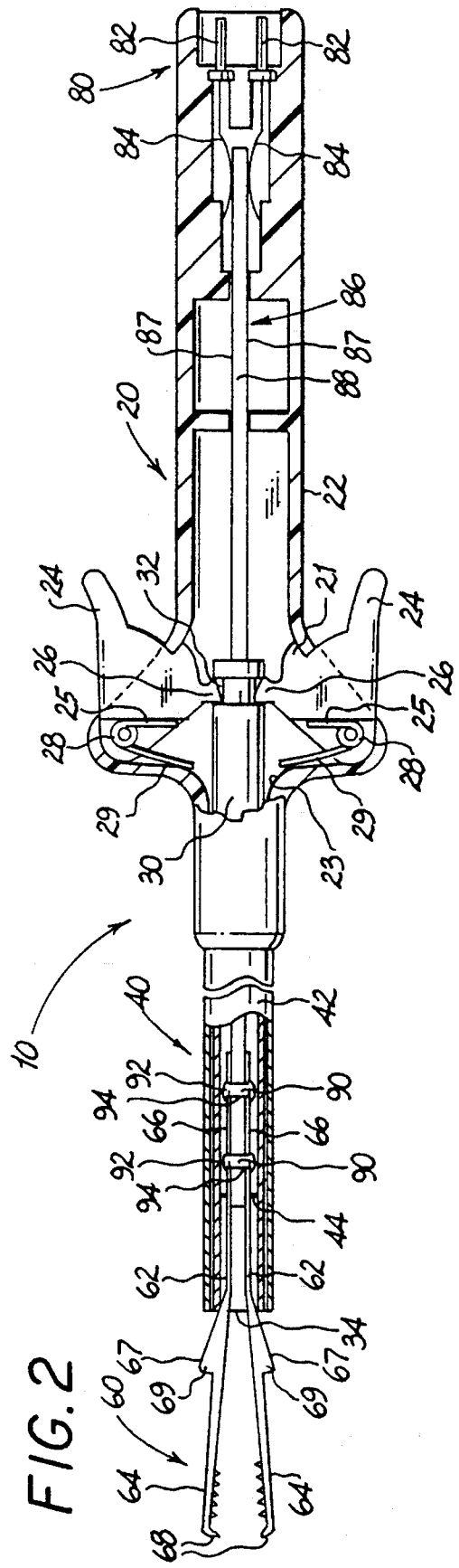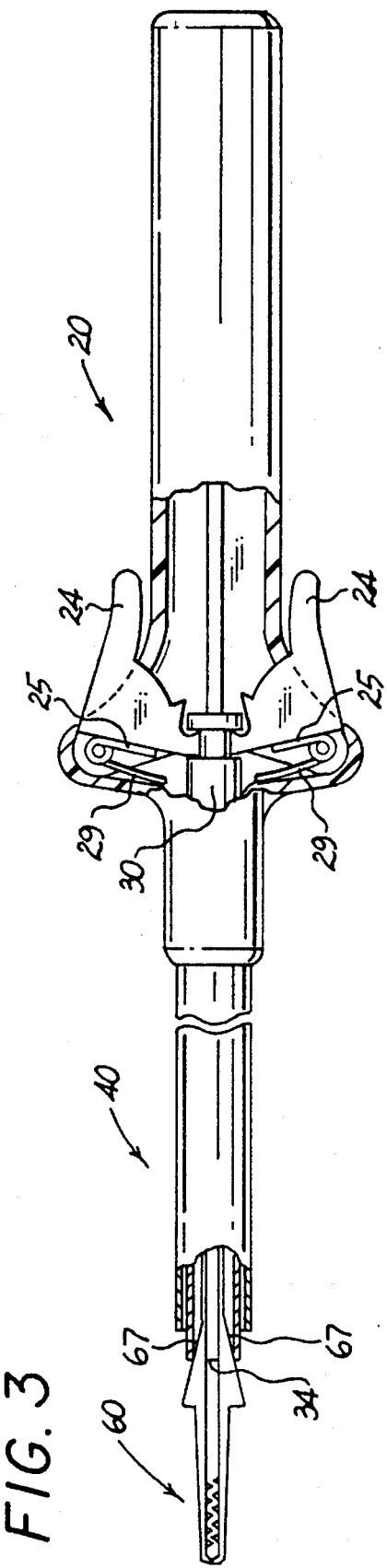
FIG. 2
FIG. 3

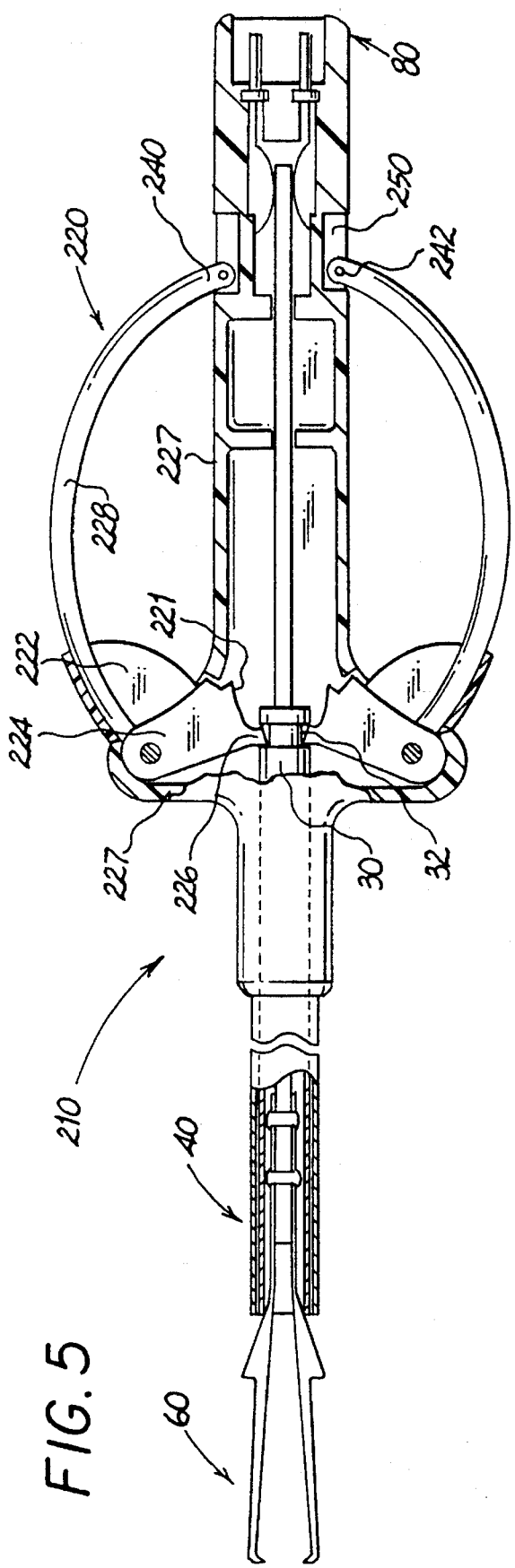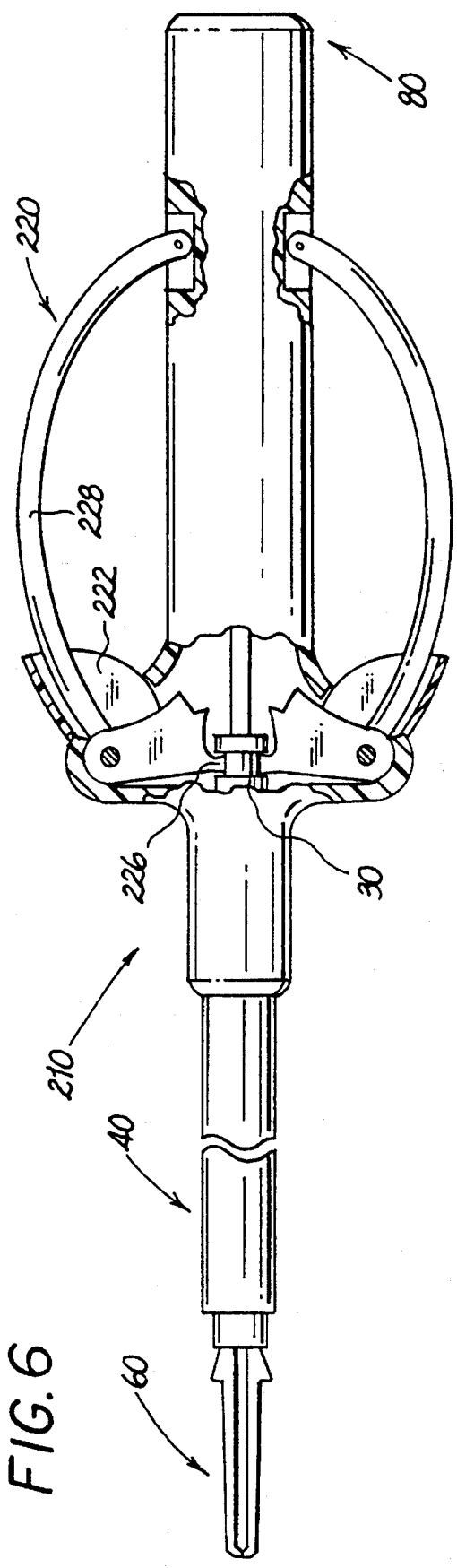

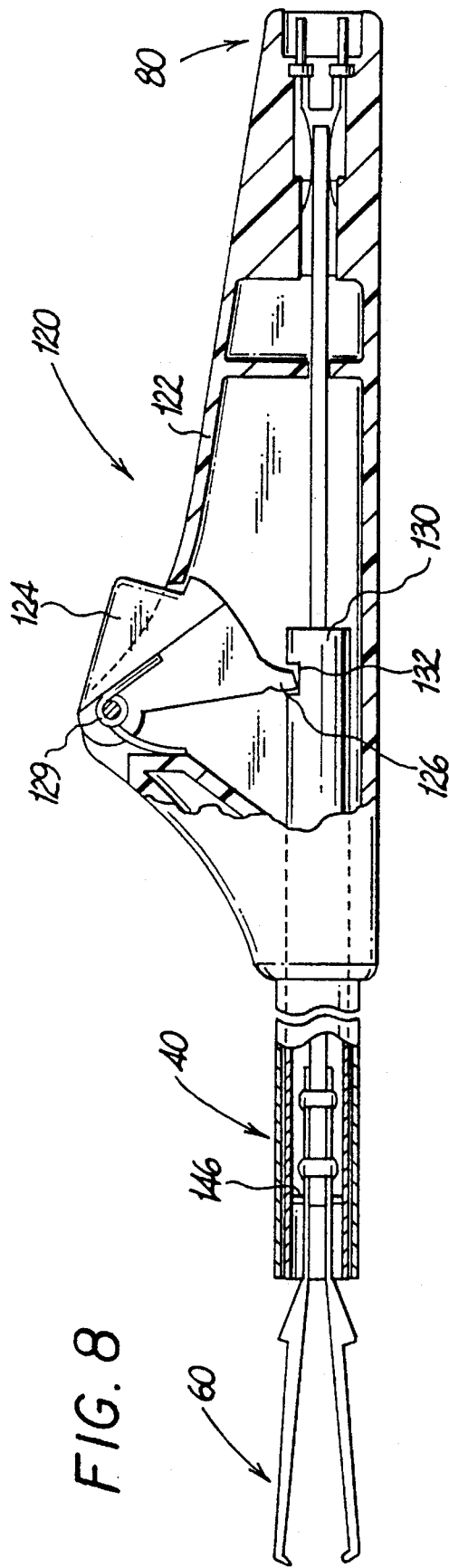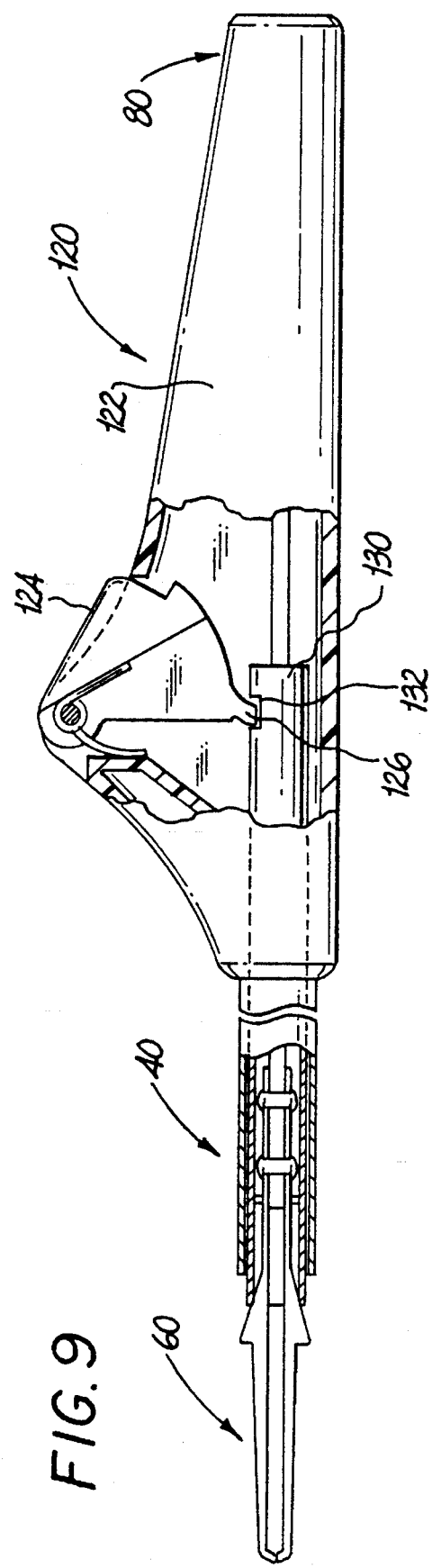

5,527,313

BIPOLAR SURGICAL INSTRUMENTS

This is a continuation of application Ser. No. 08/232,309 filed on Apr. 25, 1994, now abandoend which was a continuation of application Ser. No. 08/122,319 filed Sep. 17, 1993 now abandoned which was a continuation of application Ser. No. 07/949,581 filed on Sep. 23, 1992 now abandoned.

BACKGROUND OF THE INVENTION

1. Field of the Invention

The invention relates to bipolar surgical instruments and, more particularly, to bipolar surgical forceps for selectively grasping, manipulating, cutting and/or coagulating body tissue.

2. Description of the Related Art

Electrosurgery involves the cutting or coagulating of body tissue by application of high frequency electrical current. In bipolar electrosurgery, the electrical current is applied through an electrode which contacts the body tissue to be treated. A return electrode is placed in contact with or in close proximity to the current-supplying electrode such that an electrical circuit is formed between the two electrodes. In this manner, the applied electrical current is limited to the body tissue held between the electrodes. When the electrodes are separated from one another, the electrical circuit is open and thus inadvertent contact of body tissue with either of the separated electrodes does not cause current to flow.

To perform tissue cutting, coagulation, or a combination thereof, a high frequency power supply is connected to the bipolar instrument. Each electrode of the bipolar instrument is electrically isolated within the instrument and is separately connected to the high frequency power supply. Typical power supplies such as the SSE2L™ available from Valleylab, Inc. of Boulder, Colo., are r.f. generators which can produce different electrical waveforms to effect various electrosurgical procedures. A waveform of continuous sinewaves alternating from positive to negative at the operating frequency of the r.f. generator is employed to cut tissue. Such a waveform creates short, intense electrical sparks to rapidly heat tissue; cells are exploded and the heat dissipated as steam.

A waveform consisting of pulsating sine waves alternating from positive to negative at the operating frequency of the r.f. generator is employed to coagulate tissue. Such a waveform creates longer, less intense sparks which heat tissue less rapidly, allowing heat to be dissipated more widely than during cutting. A combination of the cutting and coagulating waveforms produces the capability to cut tissue with enhanced hemostasis over the pure cutting waveform.

A fuller description concerning the electrical aspects of electrosurgery can be found in the Valleylab SSE2L™ Instruction Manual published by Valleylab of Boulder, Colo.

Electrosurgical procedures have, in recent years, become, increasingly widespread. The ease and speed of cutting and/or coagulating tissue saves the surgeon valuable time while minimizing internal bleeding by the patient. Endoscopic and laparoscopic surgical procedures have created additional incentives for the use of electrosurgical techniques. In laparoscopic procedures, surgery is performed in the interior of the abdomen through a small incision; in endoscopic procedures, surgery is performed in any hollow viscus of the body through narrow tubes inserted through small entrance wounds in the skin. Because laparoscopic and endoscopic surgery does not bring the surgeon into direct contact with the operation site, internal bleeding must be quickly controlled by instruments easily operable from a remote location. Electrosurgical instruments provide the surgeon with the ability to electrically cut tissue such that bleeding is minimized and to effectively seal off bleeders during laparascopic and endoscopic procedures. Because laparascopic and endoscopic surgery involve considerable instrument manipulation from a remote location, the actuating mechanism must be convenient to operate once the instrument has been properly positioned.

Thus, a need exists in the art for a bipolar surgical instrument which is readily adaptable for use in laparascopic and endoscopic surgery. Such an instrument must be capable of compact design for fitting through narrow cannulas. Additionally, the instrument must be conveniently actuated by the user. A need also exists for an instrument which can be easily and reliably manufactured from inexpensive materials for single-use applications.

SUMMARY OF THE INVENTION

The present invention provides a bipolar surgical instrument comprising a handle portion, a tool portion for applying electrical energy to tissue cooperating with the handle portion for movement between an open and closed position, electrical connection means for connecting the tool portion to a source of electrical energy having receptacles for receiving the electrical energy combined with an elongated conductor for transmitting electrical energy to the tool portion, the elongated conductor having first and second conducting paths electrically isolated from one another.

More particularly, the present invention provides an endoscopic bipolar surgical forceps having a handle portion with at least one actuating handle pivotally mounted to a handle body, first and second forceps legs, each leg constituting an electrode and having a tissue gripping surface adjacent its distal end, an elongated sheath cooperating with the actuating handle to close the forceps, and electrical connection means for providing electrical energy to the forceps comprising an elongated conductor strip having first and second conducting paths separated from each other by an insulator disposed thereon.

BRIEF DESCRIPTION OF THE DRAWINGS

Preferred embodiments of the invention are described hereinbelow with reference to the drawings wherein:

FIG. 2 is a cross-sectional view of the bipolar surgical instrument of FIG. 1 showing the forceps in an open position.

FIG. 3 is a cross-sectional view of the bipolar surgical instrument of FIG. 1 showing the forceps in a closed position wherein only the tissue prongs are in contact.

FIG. 5 is a cross-sectional view of the bipolar surgical instrument according to a further embodiment of the present invention a pair of actuating handles show the forceps in an open position.

FIG. 6 is a cross-sectional view of the bipolar surgical instrument of FIG. 5 showing the forceps in a closed position.

FIG. 8 is a cross-sectional view of the bipolar surgical instrument of FIG. 7 showing the forceps in an open position.

FIG. 9 is a cross-sectional view of the bipolar surgical instrument of FIG. 7 showing the forceps in a closed position.

DETAILED DESCRIPTION OF THE PREFERRED EMBODIMENTS

Figure 1:
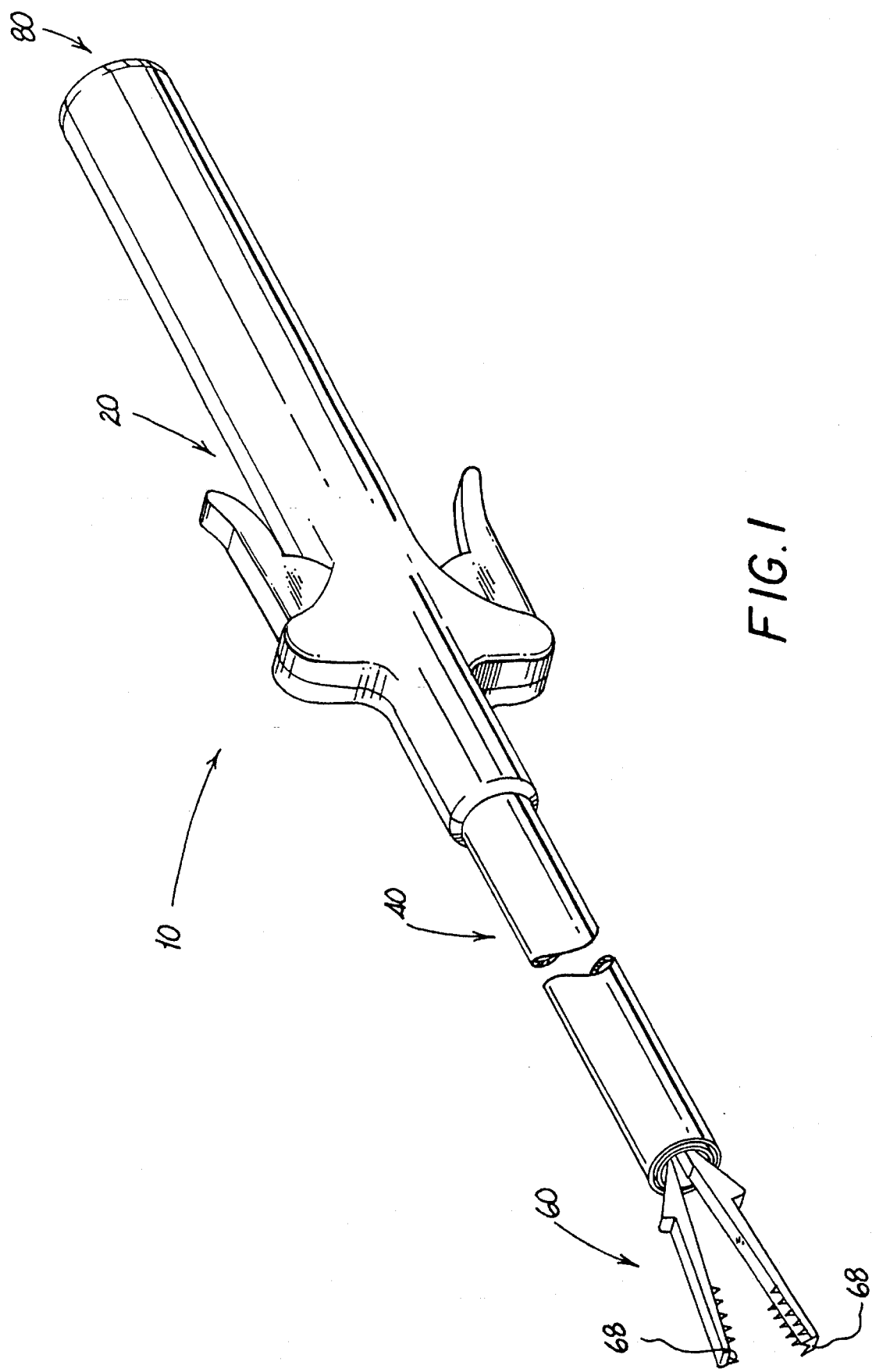
FIG. 1 is a perspective view of a bipolar surgical instrument according to one embodiment of the present invention having a pair of actuating handles.

Referring initially to FIG. 1 there is illustrated in perspective view a bipolar surgical instrument 10 according to a first embodiment of the present invention for application of electrical energy to body tissue. The instrument includes handle portion 20, endoscopic portion 40, forceps portion 60, and electrical connection portion 80.

As shown in FIG. 2, the handle portion 20 combines an elongated hollow handle body 22 with actuating handles 24 pivotally mounted thereto for opening and closing forceps 60. Each handle has a projection 26 extending into the interior of the hollow handle body. Inside handle body 22 sliding sleeve 30 engages actuating handle projections 26 through receiving slots 32. Actuation by the user translates the arcuate motion of handles 24 into longitudinal motion of sliding sleeve 30.

Handles 24 are biased to an open position (FIG. 2) through torsion springs 28 mounted within hollow handle body 22. One leg 29 of each torsion spring contacts interior wall 23 of hollow handle body 22; the other leg 25 of the torsion spring engages a retaining surface within handle 24. When the handles are actuated, legs 29 and 25 are approximated (FIG. 3), placing the torsion springs in compression. Release of handles 24 permits legs 29 and 25 to separate by action of the spring, forcing the handles to their original, open position. Handle stops 21 limit the extent to which handles 24 may open by engaging handle body interior wall 22.

A further embodiment of the bipolar surgical instrument of the present invention which employs a pair of actuating handles is shown in FIGS. 5–6. In this embodiment, actuating handles 220 comprise handle heads 224 integral with arcuate handle gripping members 228 for actuation by the user. Handle heads 224 are pivotally mounted to hollow handle body 227 within handle body shroud 222. Similar to actuating handles 24, each handle head has a projection 226 extending into the interior of the hollow handle body where it engages slot 32 of sliding sleeve 30. Actuation of handle gripping members 228 (FIG. 6) causes heads 224 to pivot, sliding sleeve 30 distally as in the previous embodiment.

At their proximal ends, handle gripping members 228 terminate in fingers 240 which are slidably received in handle slots 250. Transverse pins 242 pass through fingers 240 and have projections which engage cooperating grooves within the handle body. During handle actuation, members 228 are flattened (FIG. 6) causing pins 242 to slide proximally within their respective receiving grooves as fingers 240 slide proximally within slot 250.

Handle gripping members 228 are fabricated from a flexible, resilient material, such as polypropylene formed into a living hinge. The use of handle members 228 eliminates the need for metal handle return springs such as the torsion springs of the previous embodiment. When no force is exerted on members 228, they assume their original, arcuate configuration, pivoting heads 224 to their proximal-most position with stops 221 abutting handle wall 227. Additionally, the elongate configuration of these handles facilitates handle actuation. Regardless of the position in which the instrument is held, members 228 are easily grasped by the user to actuate the handles. The entire handle section may further be encased in a flexible polymeric material such as shrink wrap to protect handle parts and aid in user gripping.

Figure 7:
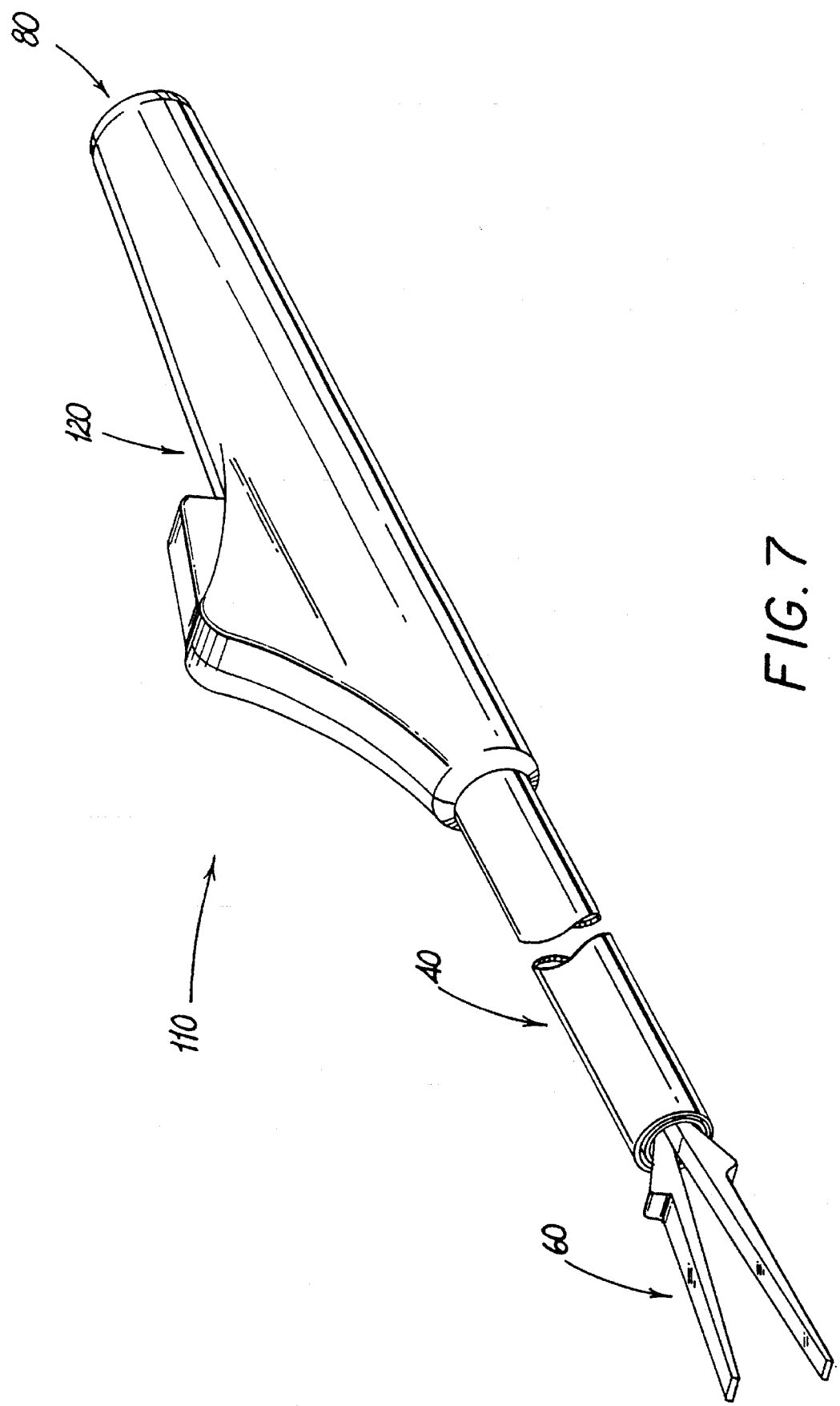
FIG. 7 is a perspective view of a bipolar surgical instrument according to a further embodiment of the present invention having a single actuating handle.
Figure 10:
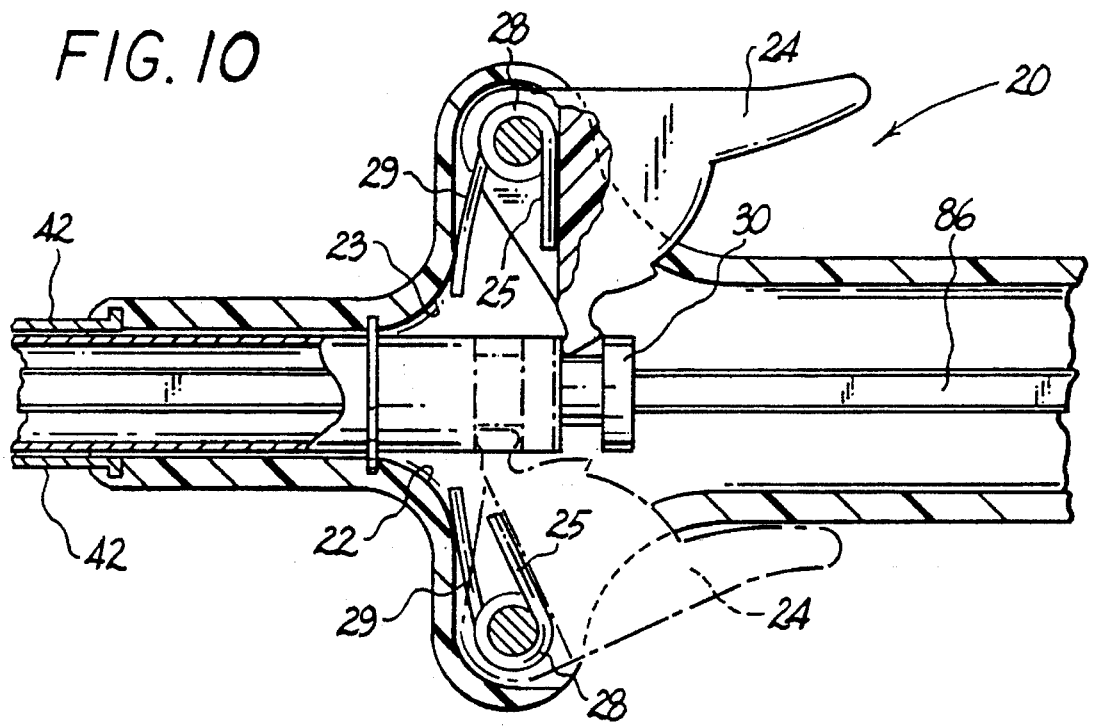
FIG. 10 is an enlarged cross-sectional view of the actuating handles of FIG. 1.
Figure 11:
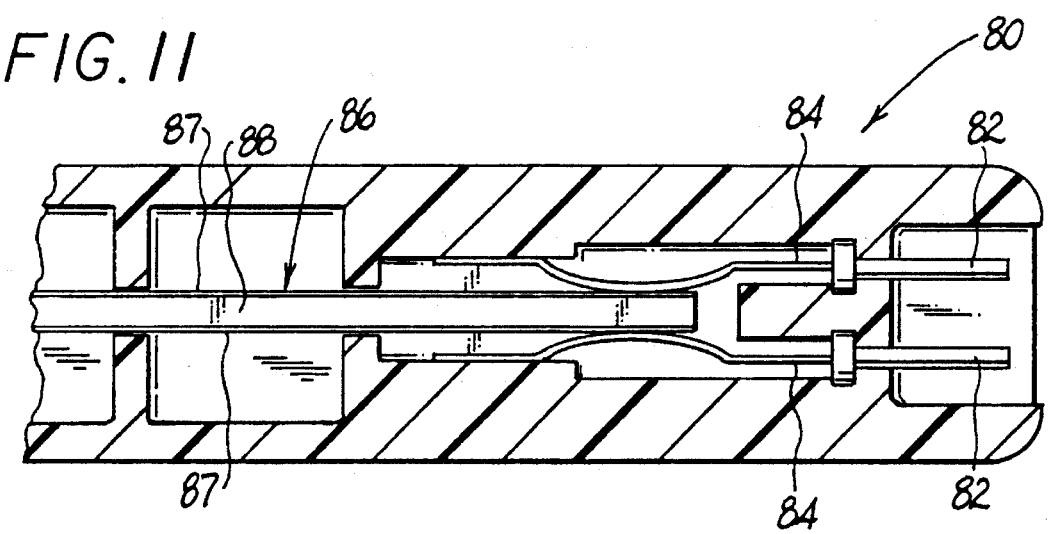
FIG. 11 is an enlarged cross-sectional view of the electrical connection portion of the surgical instrument of the present invention.
Figure 12:
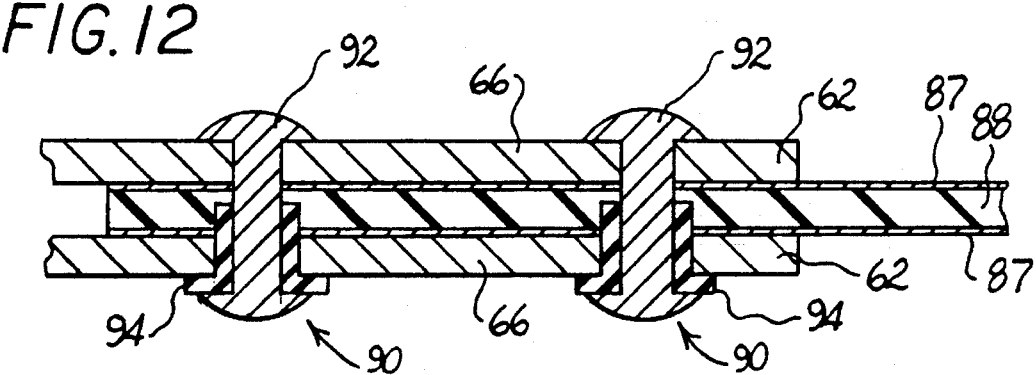
FIG. 12 is an enlarged cross-sectional view of the connection between the forceps and the conducting strip.

The bipolar surgical instrument can alternatively employ a single actuating handle, as shown in FIGS. 7–9 which illustrate a further embodiment of the present invention. FIG. 7 depicts a bipolar surgical instrument 110 having handle portion 120. Endoscopic portion 40, forceps portion 60, and electrical connection portion 80 are substantially the same as those portions of the bipolar surgical instrument depicted in FIG. 1, which will be described below. As shown in FIG. 8, handle portion 120 comprises elongated hollow handle body 122 with actuating handle 124 pivotally mounted thereto for opening and closing forceps 60. The handle has a projection 126 extending into the interior of the hollow handle body. As in the previous embodiment, projection 126 engages a sliding sleeve 130 through receiving slot 132. Torsion spring 129 biases handle 124 to an open position (FIG. 8) and is compressed during handle closure (FIG. 9).

The handles shown and described are representative handle configurations; numerous handle mechanisms may be employed. It will be appreciated that any element capable of providing longitudinal reciprocal motion to sliding sleeve 30 may be used in conjunction with the bipolar instrument of the present invention.

Alternatively, a handle mechanism can be provided which is in communication with the forceps while the sleeve remains stationary. In this configuration, the forceps move proximally and distally into and out of the stationary sleeve by action of the handles for forceps jaw closure.

The endoscopic portion 40 of the instrument includes an elongated tubular member 42 extending distally from handle portion 20. Preferably, the tubular member is fabricated from a biocompatible material such as stainless steel and coated with an insulator to prevent arcing from the electrically live forceps. Gaseous seal means 44 (FIG. 2) in the form of silicone grease or a separate seal block 146 (FIG. 8) are positioned within the endoscopic portion to prevent the escape of insufflating gases used in laparoscopic and endoscopic surgery. Sliding sleeve 30 passes into the endoscopic section tubular member 42 from the handle interior, terminating in sheath edge 34.

Forceps 60 extend from the distal end of endoscopic portion 40 and are used to transmit the electrical energy to body tissue. Forceps 60 comprise a pair of elongated forceps legs 62, preferably constructed from a biocompatible, conductive material such as stainless steel. Each forceps leg possesses a tissue-gripping jaw 64 adjacent its distal end.

Jaws 64 may be provided with serrated edges for securing tissue therebetween (FIGS. 1–4). Alternatively, the jaws may possess smooth tissue-containing surfaces for atraumatic tissue manipulation (FIGS. 5–9). Electrical power source connecting regions 66 are located adjacent the proximal end of legs 62. Regions 66 are smooth and flat to facilitate electrical connection.

Each jaw of the forceps may optionally terminate in prongs 68 (FIG. 1); one jaw possesses a centrally-disposed prong while the other jaw possesses two spaced-apart prongs. During jaw closure, the central prong of one jaw slides between the two spaced-apart prongs of the other jaw to ensure proper jaw closure alignment and thus ensure a completed electrical circuit through the desired section of tissue. Additionally, prongs 68 may be used to grip tissue during an electrosurgical procedure or, when the r.f. power supply is inactive, to position tissue as with non-electrosurgical forceps.

Proximal to the jaws each forceps leg has a projection 69 having an angled camming surface 67. As best seen in FIGS. 1 and 7, the camming surface 67 is curved. Camming surfaces 67 cooperate with distal edge 34 of sliding sleeve 30 to effect jaw closure. Because sliding sleeve 30 contacts both forceps legs, it must be fabricated from an insulating material of sufficient strength and resiliency to transmit closure force to the forceps jaws. Preferred materials include glass/polymer composites such as glass braid reinforced with epoxy.

Figure 4:
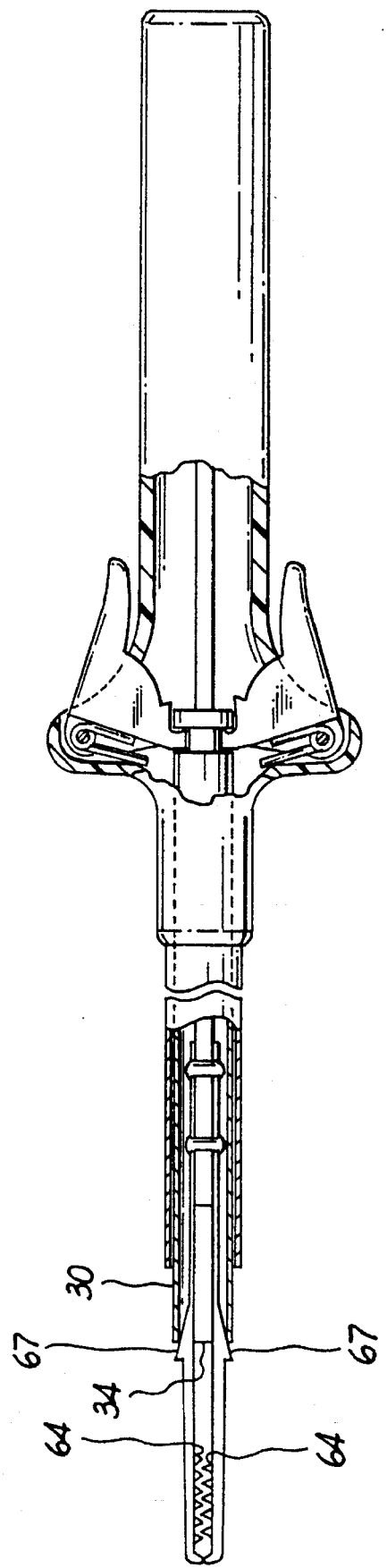
FIG. 4 is a cross-sectional view of the bipolar surgical instrument of FIG. 1 showing the forceps in a closed position wherein portions of the jaw surfaces are in contact.

When sliding sleeve 30 is pushed distally by handles 24, distal edge 34 travels along camming surfaces 67, approximating the forceps jaws. Prongs 68 are engaged while the surfaces of jaws 64 secure tissue therebetween. Note that in FIG. 3 the forceps jaws do not contact each other except for prongs 68. Further distal movement of the sleeve urges forceps jaws together along a portion of jaw surface 64 as shown in FIG. 4. Thus, the user can select the desired amount of jaw contact area, effecting a variable current density to perform a desired electrosurgical procedure.

The bipolar surgical instrument of the present invention receives power through electrical connection portion 80, located at the proximal end of handle body 22. A pair of receptacles 82 receive leads connected to an r.f. power supply. Although illustratively shown as female jacks, receptacles 82 may take the form of any conventional power connection elements, male or female, limited only by the need for compatibility with the connection elements of the power supply.

The r.f. power supply to be used with the bipolar surgical instrument may be selected from a variety of those commercially available, such as the SSE2L™ power supply from Valleylab, Inc. of Boulder, Colo. The SSE2L™ power supply is representative of preferred power sources which include cut, coagulation and blend (a blended waveform of cut and coagulation) modes, offering the user a wide range of electrosurgical options.

Extending distally from receptacles 82 and electrically connected thereto are conducting contact springs 84. Contact springs 84 engage a centrally disposed conducting strip 86 to transmit r.f. power to the forceps jaws. The use of contact springs eliminates the need for conventional solder connections, advantageously simplifying manufacture of the bipolar instrument while increasing its reliability.

Conducting strip 86 provides a pair of conducting paths 87 separated by an insulator 88. Each contact spring and each corresponding forceps leg contacts only one of these conducting paths, maintaining electrical isolation of each forceps leg prior to jaw closure. In a preferred embodiment, conducting strip 86 is fabricated from a printed circuit board, each surface of which is preferably plated with copper and overplated with nickel to form conducting paths 87; the circuit board itself forms insulator 87. Although conducting strip 86 is shown as flat, other geometries may be readily used. For example, an insulating tube having inner and outer surfaces plated with a conductor to form the two conducting paths may be employed. The shape of the conducting strip will be dictated by the type of tool selected for use at the distal end.

The use of a single element, conductor strip 80, to provide both conductor paths, greatly simplifies instrument construction. Only a single channel, which may be centrally disposed within the instrument, is necessary to supply power to the forceps jaws. Such a configuration facilitates adaptation of the bipolar instrument to endoscopic applications where the working elements must fit within a narrow endoscopic tube. Insulation is simplified since there is no opportunity for individual power-supplying wires to cross one another, short-circuiting the instrument.

Conducting strip 86 extends from the electrical connection portion 80 through sliding sleeve 30 in the handle portion 20, terminating within sleeve 30 in the endoscopic section 40 where it supplies power to the forceps jaws. To connect the forceps legs to the conducting strip and to each other, insulated fasteners are used. In a preferred embodiment, rivets 92 pass through both forceps legs' conducting regions 66 and through conducting strip 86 disposed therebetween. To maintain electrical isolation of each leg, insulating bushings 94 are disposed about one of each of the rivet's heads such that no portion of the rivet contacts one of the forceps legs and the corresponding conducting path of the conducting strip. The shank of the bushing passes into the insulating portion 88 of the conducting strip through one conducting path, but terminates before contacting the other conducting path of the strip. In this manner, the forceps legs are mechanically, but not electrically, joined. Electrical connection of each forceps leg 62 to a conductor path 87 is made along contact region 66 as fasteners 90 push regions 66 against their corresponding conductor paths.

Although the bipolar surgical instrument of the present invention has been described in terms of forceps, it will be recognized by those of skill in the art that numerous other tool configurations may be used. For example, the forceps may be replaced by tweezers, needles, blades, biopsy cups, or the like. In short, any bipolar electrosurgical tool capable of closure by a sleeve is contemplated. When the selected tool is forceps, the forceps legs may be of unequal size. For example, the forceps leg used as the electrode for supplying power to the tissue may be of small dimensions, thus increasing the current density, while the forceps leg used as the return electrode may be of larger dimensions. Such an instrument provides enhanced cutting capabilities.

The surgical instrument of the present invention may also be used for non-electrosurgical procedures. For example, the r.f. power supply can be turned off or the r.f. power supplying leads may be disconnected from the electrical connection receptacles. Thus, conventional use of a surgical tool, such as forceps, may be made with electrosurgical use optional. Such a capability is advantageous in endoscopic or laparoscopic operations since a change of instruments through the cannula would not be necessary when opting to quickly perform an electrosurgical procedure.

While the invention has been particularly shown and described with reference to the preferred embodiments, it will be understood by those skilled in the art that various modifications and changes in form and detail may be made without departing from the scope and spirit of the invention. Accordingly, modifications such as those suggested above, but not limited thereto, are to be considered within the scope of the invention.

What is claimed is:

1. A bipolar surgical instrument comprising:

at least one handle;

tool means having first and second jaw members;

movable means extending between said at least one handle and said tool means, said movable means being movable in response to movement of said at least one handle for movement of said tool means between open and closed positions to apply electrical energy to tissue;

electrical connection means for connecting said tool means to a source of electrical energy, said electrical connection means having means for receiving said electrical energy, an elongated conductor member cooperating therewith for transmitting said electrical energy, said elongated conductor member comprising a printed circuit having first and second conducting paths, said first and second conducting paths being electrically isolated from one another wherein said first jaw member electrically communicates with said first conducting path and said second jaw member electrically communicates with said second conducting path.

2. A bipolar surgical instrument as recited in claim 1 wherein said tool means comprises forceps.

3. A bipolar surgical instrument as recited in claim 1 wherein said electrical connection means further comprises contact springs extending from said means for receiving electrical energy for connecting said elongated conductor member to said means for receiving electrical energy.

4. A bipolar surgical instrument as recited in claim 1 wherein said movable means comprises sleeve means for moving said tool means between open and closed positions.

5. A bipolar surgical instrument as recited in claim 4 wherein said at least one handle comprises an actuating handle pivotally mounted to a handle body, said actuating handle having means to engage said sleeve means whereby pivotal movement of said actuating handle produces longitudinal movement of said sleeve means between open and closed positions.

6. A bipolar surgical instrument comprising:

forceps having first and second legs, each leg constituting an electrode and having means for gripping tissue adjacent its distal end;

electrical connection means for providing electrical energy to said forceps, said electrical connection means including an elongated conductor strip comprising a printed circuit having first and second conducting paths electrically isolated from one another, said first forceps leg electrically communicating with said first conducting path and said second forceps leg electrically communicating with said second conducting path; and means for closing said forceps.

7. A bipolar surgical instrument as recited in claim 6 wherein said means for gripping tissue comprises a jaw having a serrated surface.

8. A bipolar surgical instrument as recited in claim 7 wherein said means for closing said forceps comprises a handle assembly having at least one actuating handle pivotally mounted to a handle body, said actuating handle having means to engage a sliding sleeve, said sliding sleeve including a distal camming portion adapted to engage said angled camming surfaces of the first and second forceps projection.

9. A bipolar surgical instrument as recited in claim 8 wherein said handle means comprises a pair of pivotally mounted handles, each of said handles having a projection engaging said sliding sleeve.

10. A bipolar surgical instrument as recited in claim 6 wherein said first and second forceps legs further comprise projections having angled camming surfaces.

11. A bipolar surgical instrument as recited in claim 6 wherein said electrical connection means further comprises a pair of receptacles adapted to connect to an r.f. power supply.

12. A bipolar surgical instrument as recited in claim 11 wherein said electrical connection means further comprises a pair of contact springs extending from said receptacles, each spring being adapted to contact one of said first and second conducting paths of said elongated conductor strip to supply electrical energy thereto.

13. A bipolar surgical instrument as recited in claim 6 wherein said conductor strip comprises a printed circuit having said first and second conducting paths disposed about an insulating member.

14. A bipolar surgical instrument as recited in claim 6 further comprising insulated fastening means for connecting said conductor strip to said first and second forceps legs.

15. An endoscopic bipolar surgical instrument comprising:

a handle assembly;

an elongated tubular member having a longitudinal axis and connected to said handle assembly;

movable means positioned within said elongated tubular member and coupled to said handle assembly;

a gaseous seal within said elongated tubular member;

first and second jaw members extending from a distal end of said tubular member and movable by said movable means between an electrically inactive open position and a closed position to apply electrical energy to tissue; and electrical connection means for connecting said jaw members to a source of electrical energy, said electrical connection means comprising means for receiving said electrical energy, an elongated conductor member cooperating therewith for transmitting said electrical energy, said elongated conductor member extending longitudinally within said tubular member and terminating at a position between said first and second jaw members, said conductor member comprising a printed circuit having first and second conducting paths electrically isolated from one another said first jaw member electrically communicating with said first conducting path and said second jaw member electrically communicating with said second conducting path.

16. A bipolar surgical instrument as recited in claim 15 wherein said first and second jaw members comprises forceps.

17. A bipolar surgical instrument as recited in claim 16 wherein said forceps comprises first and second forceps legs, each forceps leg having serrated gripping surfaces adjacent its distal end.

18. A bipolar surgical instrument as recited in claim 16 wherein said forceps includes alignment means.

19. A bipolar surgical instrument as recited in claim 18 wherein said alignment means includes inter-engaging prongs at the distal end of said forceps.

20. A bipolar surgical instrument as recited in claim 15 wherein said electrical connection means further comprises contact springs extending from said means for receiving electrical energy for connecting said elongated conductor member to said means for receiving electrical energy.

21. A bipolar surgical instrument as recited in claim 15 wherein said movable means comprises sleeve means cooperating with said handle assembly for moving said jaw members between said open and closed positions.

22. A bipolar surgical instrument as recited in claim 21 wherein the handle assembly comprises at least one pivotal actuating handle having means to engage said sleeve means whereby pivotal movement of said actuating handle translates to longitudinal movement of said sleeve means for moving said tool means between said open and closed positions.

23. A bipolar surgical instrument comprising:

an elongated tubular member;

at least one handle extending from said tubular member;

a movable sleeve positioned within said elongated member and operatively connected to said at least one handle;

first and second jaw members at least partially disposed within said tubular member and extending from a distal end thereof, wherein movement of said at least one handle moves said sleeve to move said first and second jaw members between open and closed positions; and elongated conductive means extending longitudinally within said elongated tubular member and having a proximal end for receiving electrical energy from an electrical energy source, said conductive means being positioned between said first and second jaw members and forming a first conductive path between said electrical energy source and said first jaw member and forming a second conductive path between said electrical energy source and said second jaw member.

24. A bipolar surgical instrument as recited in claim 23 wherein said elongated conductive means is composed of a substantially rigid material.

25. A bipolar surgical instrument as recited in claim 23 wherein said elongated conductive means is substantially planar.

26. A bipolar surgical instrument as recited in claim 25 wherein said elongated conductive means is composed of an insulating central portion having first and second electrically isolated conducting paths disposed thereon.

27. A bipolar surgical instrument comprising:

first and second jaw members electrically isolated from each other, each jaw member constituting an electrode;

electrical connection means for providing electrical connection to said first and second jaw members, said electrical connection means including elongated conductor means having insulating and conducting portions, said elongated conductor means extending at least partially between said first and second jaw members wherein said insulating portion of said elongated conductor means maintains electrical isolation of said first and second jaw members.

28. A bipolar surgical instrument as recited in claim 27 wherein said elongated conductor means comprises a planar insulating member having first and second sides, a first conducting path disposed on said first side and a second conducting path disposed on said second side.

29. A bipolar surgical instrument comprising:

a handle assembly;

an elongated tubular member having a longitudinal axis and connected to said handle assembly;

a movable sleeve operatively connected to said handle assembly;

first and second jaw members extending from a distal end of said tubular member, said first and second jaw members being movable between open and closed positions in response to movement of said sleeve by movement of said handle assembly; and electrical connection means for connecting said jaw members to a source of electrical energy, said electrical connection means comprising means for receiving said electrical energy, an elongated conductor means cooperating therewith for transmitting said electrical energy, said elongated conductor means extending longitudinally within said tubular member, and comprising a printed circuit having first and second conductive paths electrically isolated from one another by at least one insulator member, said at least one insulator member terminating within said elongated tubular member, said first conductive path electrically communicating with said first jaw member and said second conductive path electrically communicating with said second jaw member.

30. A bipolar surgical instrument as recited in claim 29 wherein said handle assembly comprises at least one actuating handle pivotally mounted to a handle body, said actuating handle having means to engage said movable sleeve means whereby pivotal movement of said actuating handle translates to longitudinal movement of said sleeve means for moving said first and second jaw members between said open and closed positions.

31. A bipolar surgical instrument as recited in claim 29 wherein at least one of said electrically isolated conductive paths is disposed upon said at least one insulating member.

* * * * *